United States Patent [19]

Foote

[11] Patent Number: 4,966,564
[45] Date of Patent: Oct. 30, 1990

[54] ELECTRICAL CONNECTOR BETWEEN ELECTRODE LEADS AND PACEMAKER TERMINAL

[75] Inventor: Roger M. L. Foote, Eastwood, Australia

[73] Assignee: Telectronics, N.V., Netherlands Antilles

[21] Appl. No.: 242,349

[22] Filed: Sep. 9, 1988

[51] Int. Cl.⁵ .......................................... H01R 13/33
[52] U.S. Cl. .................................. 439/840; 439/874; 439/841
[58] Field of Search .............. 439/788, 840, 841, 843, 439/851, 799, 827, 245, 874

[56] References Cited

U.S. PATENT DOCUMENTS

| | | | |
|---|---|---|---|
| 1,553,711 | 9/1925 | Myers | 439/840 |
| 3,308,229 | 3/1967 | Burniston | 439/841 |
| 3,383,647 | 5/1968 | Duffield et al. | 439/840 |
| 4,093,337 | 6/1978 | Jacobson | 439/840 |
| 4,445,511 | 5/1984 | Cowdery et al. | |
| 4,462,657 | 7/1984 | Snowden et al. | 439/788 |
| 4,469,104 | 9/1984 | Peers-Traverton | |
| 4,540,236 | 9/1985 | Peers-Traverton | |

FOREIGN PATENT DOCUMENTS 112291  10/1925  Switzerland ..................... 439/843

Primary Examiner—David L. Pirlot
Attorney, Agent, or Firm—Finnegan, Henderson, Farabow, Garrett & Dunner

[57] ABSTRACT

Electrical connection is established between the lead electrodes and the pacemaker terminals whereby a straight length of coil spring is placed within a hole transverse to the lead hole. A portion of the transverse hole intersects the lead hole so that a portion of coil spring extends transversely into the lead hole. The ends of the coil spring section are welded on opposite sides of the terminal. Electrical connection is made as the spring contacts the ring electrode on the lead.

19 Claims, 3 Drawing Sheets a.      b.      c.      d.      e.

4,966,564

ELECTRICAL CONNECTOR BETWEEN ELECTRODE LEADS AND PACEMAKER TERMINAL

BACKGROUND OF THE INVENTION

The present invention relates to an electrical connector for a cardiac pacemaker for connecting an electrode lead to a terminal on the pacemaker.

Implantable pacemakers suitable for sensing and/or pacing cardiac functions are well known in the art. Such devices operate in conjunction with electrode leads which have a distal end that is implanted in the tissue that is to be sensed or paced, and a proximal end that is connected to the pacemaker. Specifically, the proximal end is typically coupled to a terminal provided on the pacemaker so that electrical connection may be made between the electrode lead and circuitry within the pacemaker.

A number of concerns arise regarding the coupling between the pacemaker terminal and the electrode lead. In addition to desiring electrical connection between the two structures, it is important to ensure secure mechanical connection so that the lead does not become dislodged or disconnected from the terminal. Other concerns relate to providing a connector arrangement which is convenient to use so that the physician performing implantation of the pacemaker does not have difficulties in successfully connecting the electrode lead to the pacemaker terminal.

Various arrangements for connecting the electrode lead to the pacemaker terminal have been proposed and used in the art. U.S. Pat. No. 4,540,236 to Peers-Trevarton has a comprehensive review of the different types of lead electrode to pacemaker terminal connections that have been used, and deals not only with electrical connection but also mechanical connection and sealing arrangements. Another Peers-Trevarton patent, U.S. Pat. No. 4,469,104, discloses a connector assembly incorporated into the electrodes of a multi-conductor lead which utilizes resiliant conductive rings.

Other known connection methods utilize a grub screw provided perpendicularly to the electrode lead in order to secure the lead in place in a pacemaker terminal. An example of such an arrangement is disclosed in U.S. Pat. No. 4,445,511 to Cowdery et al.

Many of these different connection arrangements do not fully satisfy the various concerns outlined above, however. Some of the arrangements are complicated to manufacture or are inconvenient to use. Others require more space than is available in modern pacemakers, particularly pacers having relatively thin dimensions. Accordingly, a need still exists for a connection arrangement that is responsive to the various concerns associated with impantation or explantation of pacemakers.

SUMMARY OF THE INVENTION

It is an object of the invention to connect an electrode lead to a pacemaker terminal without need for a set or grub screw as a means of electrical connection.

Another objection of the invention is to provide a connector for an electrode lead and pacemaker terminal that involves minimal space and requires less manufacturing effort than conventional connectors.

Additional objects and advantages of the invention will be set forth in part in the description which follows and in part will be obvious from the description or may be learned by practice of the invention. The objects and advantages of the invention may be realized and attained by means of the instrumentalities and combinations particularly pointed out in the appended claims.

To achieve the objects and in accordance with the purpose of the inventions, as embodied and broadly described herein, the invention includes a terminal having a transverse passageway for receiving an electrode lead and a connector for coupling the electrode lead to the terminal, the connector comprising canted coil spring means intersecting the transverse passageway in the terminal for coupling the electrode lead within the hole; and means for securing the spring means to the terminal.

According to a first embodiment of the invention, a terminal assembly for an implantable heart pacemaker device for connection to an electrode lead comprises: a terminal body having a generally cylindrical shape and including a first transverse passageway for receiving the electrode lead and a second transverse passageway intersecting the first passageway; and a canted coiled spring disposed within the second passageway and tangentially engaging the electrode lead upon insertion of the lead into the first passageway, the ends of the spring being secured to the terminal body by spot welding.

According to a second embodiment of the invention, a terminal assembly for an implantable heart pacemaker device for connection to an electrode lead comprises: a terminal body having a generally cylindrical shape, including a transverse passageway for receiving the electrode lead and a circumferential groove substantially adjacent the ends of the passageway; and a canted coil spring disposed circumferentially about the terminal body within the groove, the spring securedly engaging the electrode lead when inserted into the transverse passageway in the terminal body.

The accompanying drawings, which are incorporated in and constitute part of this specification, illustrate presently preferred embodiments of the invention and, together with the following description, serve to explain the principles of the invention.

DESCRIPTION OF THE PREFERRED EMBODIMENTS

Figure 1:
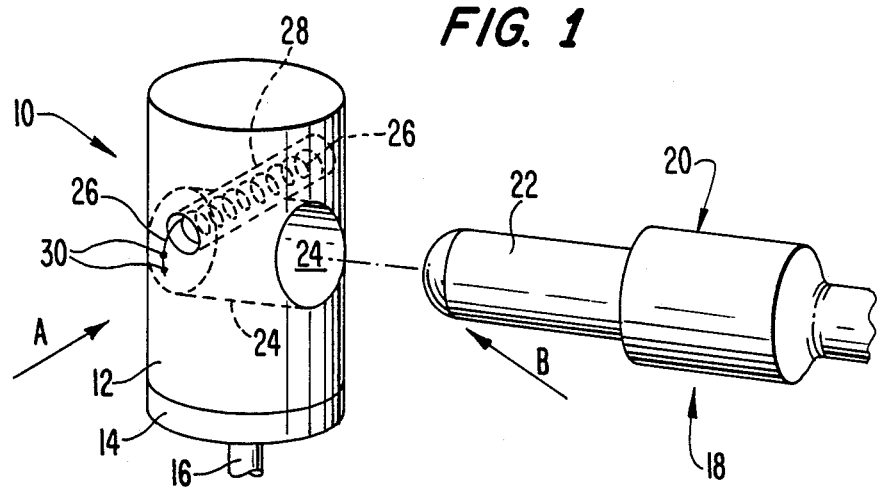
FIG. 1 is a perspective view, including interior details, of a connector assembly for a pacemaker terminal and electrode lead according to a first embodiment of the present invention.

Reference will now be made in detail to the presently preferred embodiments of the invention, examples of which are illustrated in the accompanying drawings. Through the drawings, like reference characters are used to designate like elements.

FIG. 1 is a perspective view, including partial interior details, of a pacemaker terminal having a connector assembly according to the present invention. The pacemaker terminal is generally designated by reference character 10 and includes a terminal body 12 formed of a conductive material, such as titanium, tivanium or other conductor suitable for conveying electrical signals. Terminal body 12 is mounted on a pacemaker (not shown) via a ceramic insulating portion 14 and is electrically connected to circuitry (not shown) within the pacemaker via a feedthrough lead 16. Lead 16 is also conductive and may be integrally formed with terminal body 12, if desired.

Arrangements and materials suitable for providing a terminal body, insulating portion and feedthrough lead of the type described above, as well as for connecting such structures to a pacemaker, are known in the art and need not be described further for purposes of understanding the present invention. Variations may be made in these structures, such as elimination of the insulating portion, as desired without departing from the scope of the claimed invention.

Pacemaker terminal 10 is intended to couple electrically and mechanically with an electrode lead, generally designated by reference character 18 in FIG. 1. Lead 18 has a distal end (not shown) suitable for implantation in tissue so as to provide sensing or pacing thereof, and a proximal end suitable for connection to terminal 10. The proximal end of lead 18 is indicated by reference character 20 in FIG. 1 and includes a conductive tip 22. Electrode leads of the type described herein are well known in the art and may be variously employed with the disclosed connector assembly without departing from the spirit or scope of the claimed invention.

Figure 2:
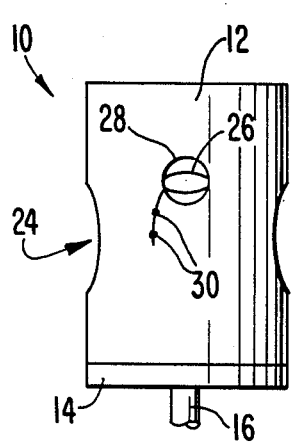
FIG. 2 is a side plan view of the connector assembly of FIG. 1 taken in the direction of arrow A.
Figure 3:
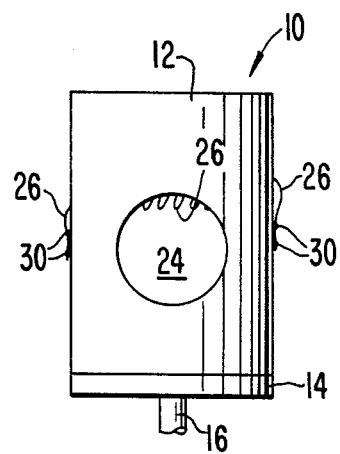
FIG. 3 is a side plan view of the connector assembly of FIG. 1 taken in the direction of arrow B.

According to the present invention, terminal body 12 includes a transverse passageway 24, as shown in perspective view in FIG. 1 and in cross-sectional views in FIGS. 2-3, having an interior diameter sufficient to permit insertion of tip 22 of electrode lead 18. Preferably, the diameter of passageway 24 is only slightly greater than that of tip 22. The particular arrangement for connecting tip 22 with terminal body 12, once inserted into place in passageway 24, will be described hereinbelow with reference to FIGS. 1-3.

In accordance with the invention, canted coil spring means are provided intersecting the transverse passageway in the terminal for coupling the electrode lead within the hole. As embodied herein and shown in FIGS. 1-3, the spring means are designated by reference character 26 and comprise a straight length of a canted coil spring. The spring is formed of an electrically conductive material which is biocompatible in nature. Spring 26 is disposed within a second passageway 28 provided in terminal body 12 so as to intersect, at least in part, first passageway 24. In the embodiment illustrated in FIGS. 1-3, for example, passageway 24 extends substantially halfway into passageway 28, i.e., through its diameter. Other degrees of intersection may be utilized, however, without departing from the spirit or scope of the invention.

As best shown in FIGS. 2 and 3, passageway 28 is disposed transverse to passageway 24. As will be appreciated from the following description, variations in the placement of passageway 28 relative to passageway 24 may be made. For example, passageway 28 may be disposed vertically across passageway 24 or at an angle thereto or at another orientation.

The present invention also provides for means for securing the spring means to the terminal. As embodied herein and shown best in FIGS. 1 and 3, the securing means prefereably comprise spot welds, designated generally by reference character 30. Spot welds 30 are used to securely affix the ends of spring 26 to terminal body 12 adjacent both outer openings of passageway 26. Arrangements other than spot welding can be used to secure spring 26 in this fashion, however, without departing from the spirit or scope of the invention. For example, solder, glue, brazing or other known techniques could be employed so as to securedly couple the ends of spring 26 to terminal body 12.

In use, tip 22 of electrode lead 18 is inserted into passageway 24 of terminal body 12. During this operation, tip 22 comes into tangential contact with spring 26 due to the intersection of passageways 26 and 24, and the contacted portion of spring 26 is resiliently depressed by the tangential interposition of tip 22. Spring 26 counters this deformation by exerting pressure onto that portion of tip 22 in contact with the spring. In this fashion, spring 26 serves to mechanically hold tip 22 in place via direct pressure upon tip 22 as well as by pressing tip 22 against the inner surface of passageway 24. Electrical contact is also maintained via the compression of spring 26 against tip 22 and the inner surface of passageway 24, thus providing for effective electrical conduction between electrode lead 18 and terminal body 12. The cant of the spring allows the crosssectional dimension of the coils of the spring to be suitably reduced so as to accommodate the imposition of the electrode lead, as described.

Figure 4A:
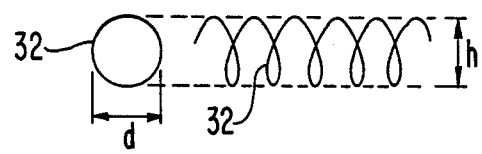
FIGS. 4a–4c are side and end plan views of a normal spring, a canted spring having an elliptical cross section and a canted spring having a circular cross section, respectively.
Figure 4B:
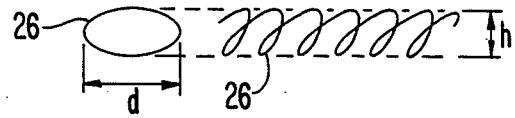
Figure 4C:
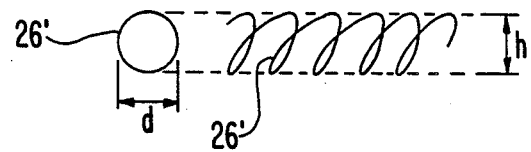

Details of spring 26 will now be explained with specific reference to FIGS. 4 and 5. FIG. 4a shows, in side plan view and in end plan view, a normal (uncanted) spring 32. FIG. 4b shows the same views of a canted spring 26 having an elliptical cross section, and FIG. 4c shows these views of a canted spring 26' having a circular cross section. In a normal spring, such as spring 32 of FIG. 4a, the coils of the spring are substantially upright and the height (h) is equal to the cross-sectional diameter (d). In a canted spring, such as springs 26 and 26' of FIGS. 4b and 4c, respectively, the coils are disposed at an angle rather than being substantially upright.

In an elliptical canted spring, such as spring 26 of FIG. 4b, the height (h) of the spring is less than its cross-sectional dimension (d). Such a spring can be manufactured by partially flattening a normal spring, thereby producing both a canted angle and an elliptical shape for the coils of the spring. In a circular canted spring, as shown by spring 26' in FIG. 4c, the height (h) is substantially equal to the cross-sectional diameter (d) even though the coils are disposed at an angle. Such a spring could be manufactured by starting with an elliptical canted spring and then flattening it in the direction of the long axis of the elliptical coils until the spring assumes a circular cross section. Other manufacturing arrangements can be employed for producing these canted springs, however, without departing from the spirit or scope of the invention.

A presently preferred embodiment utilizes an elliptical canted spring having cross--sectional width and height dimensions of 0.79 mm and 0.635 mm, respectively. The spring is formed of a coiled wire element having a thickness of 0.098 mm. Other sizes and canted spring shapes can be embployed, however, as described herein without departing from the spirit or scope of the invention.

Figure 5:
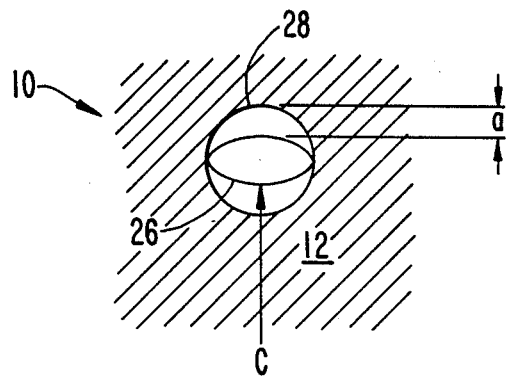
FIG. 5 is an end plan view of a canted spring in a circular hole of the pacemaker terminal shown in FIG. 1.

FIG. 5 illustrates the effect of the terminal pin of an electrode lead (not shown) upon spring 26 within passageway 28 in terminal body 12. Arrow C diagrammatically shows the direction of force exerted by the terminal pin as the proximal end of the electrode lead is introduced into lead passageway 24 (not shown) and encounters spring 26. As contact is made between the terminal pin and spring 26, the spring is deformed and the distance between the spring and the inner surface of passageway 28, i.e., dimension a, is reduced. Effective electrical connection between the terminal pin, spring 26 and terminal body 12 is established by these elements contacting each other in the described manner.

Spring 26 shown in FIG. 5 is elliptical in cross section, such as that shown in FIG. 4b. As an alternative, a canted spring having a circular cross section could be employed, such as that shown in FIG. 4c and indicated by reference character 26'. Use of such a spring 26' would result in distance a being smaller since the circular cross section of the spring would correspond more closely to the circular shape of passageway 28 than the arrangement shown in FIG. 5. In other words, spring 26' would yield a closer fit within a circular passageway 28 than does spring 26. Additionally, since the diameter of spring 26' may be smaller than the longer axis of the ellipse of spring 26, a smaller diameter passageway 28 can be employed in order to house the spring. All of these factors contribute to effective electrical coupling between the terminal pin, spring and terminal body when the electrode lead is inserted into the pacemaker terminal.

Figure 6:
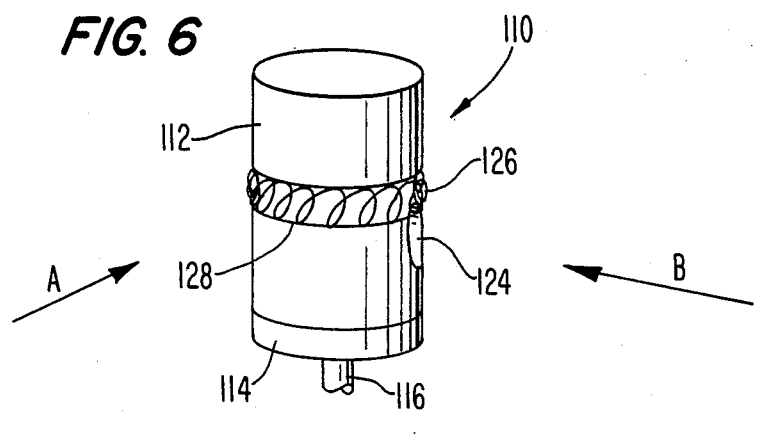
FIG. 6 is a perspective view of a pacemaker terminal having a connector assembly in accordance with a second embodiment of the present invention.
Figure 7:
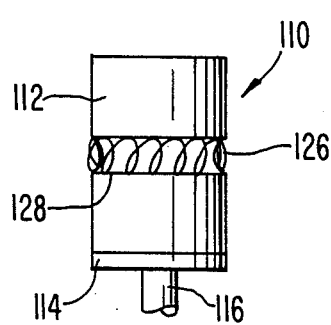
FIG. 7 is a side plan view of the pacemaker terminal of FIG. 6 taken in the direction of arrow A.
Figure 8:
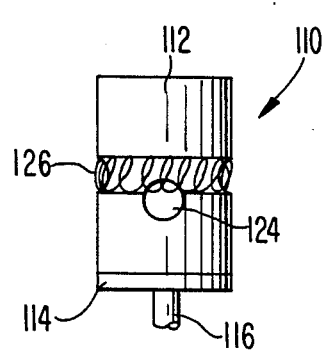
FIG. 8 is a side plan view of the pacemaker terminal of FIG. 6 taken in the direction of arrow B.

A second embodiment of a connector apparatus according to the present invention will now be described with reference to FIGS. 6-8. Terminal 110 includes a terminal body 112, insulating portion 114 and feedthrough lead 116 of the type described above with respect to terminal 10 of FIGS. 1-3. Terminal body 112 has a transverse passageway 124 adapted to receive the terminal pin of the proximal end of an electrode lead (not shown) of the type described above. For purposes of brevity, a discussion of these common elements will not be repeated and the following description chiefly focuses on the features which serve to distinguish this second embodiment.

In this second embodiment, terminal body 112 according to the present invention includes a circumferential groove 128 located substantially adjacent the ends of passageway 124. Also according to the invention, a canted coil spring 126 is provided which is disposed circumferentially about the terminal body 112 within groove 128. As shown best in FIG. 8, spring 126 and groove 128 are positioned so that the inner surface of passageway 124 extends approximately halfway into the width of groove 128. Thus, a portion of spring 126 projects into the space defined by passageway 124. Other spacial arrangements for projecting spring 126 into the interior region of passageway 124 may be utilized, however, without departing from the spirit or scope of the invention.

Upon insertion of the terminal pin of an electrode lead (not shown in FIGS. 6-8) into passageway 124, the terminal pin comes into contact with spring 126. Because the spring exerts a counterforce against such contact, the terminal pin is thereby electrically connected to the spring and to the terminal body 112 on which the spring is disposed.

Spring 126 can completely surround terminal body 112, in which case the terminal pin will contact portions of the spring at both ends of passageway 124. In such a case, the spring can be made continuous in nature, i.e., having ends that are welded together to form a continuous circular spring. Another benefit of this arrangement is that the spring will cant in opposite directions at the two ends of passageway 124, thereby minimizing possible rotation of the terminal pin and electrode lead. However, other arrangements may be employed for mounting a spring so as to provide the described contact with the terminal pin. For example, spring 126 need not fully encircle terminal body 112, i.e., the circumferential sections of spring 126 would be provided only in the vicinity of the ends of passageway 124. Alternately, the spring need not be located at both ends of passageway 124, but instead be positioned only at one end thereof.

Two or more canted springs may also be provided in the embodiments of FIGS. 1-3 and FIGS. 6-8, according to the present invention. Thus, additional passageways 28 with springs 26 may be included in terminal body 12 of FIGS. 1-3, as could additional springs 126 and grooves 128 be provided in terminal body 112 of FIGS. 6-8. These additional elements could be disposed so as to project into the lead passageway (24 or 124) from different areas, e.g., above and below the terminal pin, or at different orientations, e.g., at an angle to each other. Variations of this type are considered to be within the spirit and scope of the present invention.

Figure 9:
FIG. 9a–9e are cross-sectional views of various wires for forming a canted spring for use in a pacemaker terminal connector assembly according to the present invention.
Figure 9:
Figure 9:
Figure 9:
Figure 9:

The canted spring may be formed of wire having a circular cross section, as shown in FIG. 9a. To achieve efficient contact between the spring and electrode lead, the spring can be manufactured with edges. For example, the spring can be made from wire having a square, rectangular, star-shaped or polygonal cross section, as illustrated in FIGS. 9b-9e, respectively. Other shapes providing edges for the spring may also be used.

The structure described herein may be used to electrically connect the tip electrode of an electrode lead to a pacemaker. It also may be used to electrically connect the pacemaker to a ring electrode on the electrode lead. Accordingly, the connector structure of the present invention is not limited to connecting only the tip of the lead, but rather can also be used to connect to other electrodes on the lead.

Other embodiments of the invention will be apparent to those skilled in the art from consideration of the specification and practice of the invention disclosed herein. Thus, it is intended that the specification and drawings be considered as exemplary only, with the true scope and spirit of the invention being indicated by the following claims.

What we claim is:

1. A terminal assembly for an implantable heart pacemaker device for connection to an electrode lead, comprising:

a conductive terminal body having a first transverse passageway for receiving the electrode lead and a second transverse passageway extending completely through said body and intersecting the first passageway; and canted coiled spring means disposed within the second passageway for tangentially engaging the electrode lead upon insertion into the first passageway, said spring means having ends which protrude at both ends of the second passageway and are secured to the outer surface of said terminal body.

2. The terminal assembly as recited in claim 1, wherein the second passageway is disposed substantially transverse to the first passageway.

3. The terminal assembly as recited in claim 1, wherein said spring means comprises a canted spring having a circular cross section.

4. The terminal assembly as recited in claim 1, wherein said spring means comprises a canted spring having an elliptical cross section.

5. The terminal assembly as recited in claim 1, wherein said spring means is formed of a wire having a circular cross section.

6. The terminal assembly as recited in claim 1, wherein said spring means is formed of a wire having a square cross section.

7. The terminal assembly as recited in claim 1, wherein said spring means is formed of a wire having a rectangular cross section.

8. The terminal assembly as recited in claim 1, wherein said spring means is formed of a wire having a star shaped cross section.

9. The terminal assembly as recited in claim 1, wherein said spring means is formed of a wire having a polygonal cross section.

10. A terminal assembly for an implantable heart pacemaker device for connection to an electrode lead, comprising:

a terminal body having a transverse passageway for receiving the electrode lead and a circumferential groove disposed on the outer surface of said terminal body substantially adjacent at least one end of the passageway; and canted coil spring means disposed on said terminal body within said groove for securely engaging the electrode lead when inserted into the transverse passageway in said terminal body, said groove and said canted coil spring means lying in a common plane that is substantially parallel to the transverse passageway.

11. The terminal assembly as recited in claim 10, wherein said spring means comprises a canted spring having a circular cross section.

12. The terminal assembly as recited in claim 10, wherein said spring means comprises a canted spring having an elliptical cross section.

13. The terminal assembly as recited in claim 10, wherein said spring means is formed of a wire having a circular cross section.

14. The terminal assembly as recited in claim 10, wherein said spring means is formed of a wire having a square cross section.

15. The terminal assembly as recited in claim 10, wherein said spring means is formed of a wire having a rectangular cross section.

16. The terminal assembly as recited in claim 10, wherein said spring means is formed of a wire having a star-shaped cross section.

17. The terminal assembly as recited in claim 10, wherein said spring means is formed of a wire having a polygonal cross section.

18. The terminal assembly as recited in claim 10, wherein said groove extends circumferentially completely around said terminal body adjacent both ends of the passageway.

19. The terminal assembly as recited in claim 18, wherein said spring means is disposed circumferentially about said terminal body for engaging the electrode lead, at both ends of the transverse passageway, upon insertion of the electrode lead into the transverse passageway.

* * * * *